US00PP26655P2

(12) United States Plant Patent
Wood

(10) Patent No.: US PP26,655 P2
(45) Date of Patent: Apr. 26, 2016

(54) ***SPIRAEA* PLANT NAMED 'SMSMBK'**

(50) Latin Name: *Spiraea media*
Varietal Denomination: SMSMBK

(71) Applicant: Timothy D. Wood, Spring Lake, MI (US)

(72) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 15 days.

(21) Appl. No.: 14/121,372

(22) Filed: Aug. 26, 2014

(51) Int. Cl.
*A01H 5/00* (2006.01)

(52) U.S. Cl.
USPC ..... Plt./226

(58) Field of Classification Search
USPC ..... Plt./226
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Spiraea* plant named 'SMSMBK', characterized by its compact, upright, outwardly spreading and mounding plant habit; vigorous growth habit; freely branching habit; dense and bushy habit; developing leaves that are greyed orange in color becoming medium green with a greyed green-colored overlay with development; large inflorescences with white-colored flowers; good garden performance; and resistance to mildew pathogens.

3 Drawing Sheets

Botanical designation: *Spiraea media.*
Cultivar denomination: 'SMSMBK'.

BACKGROUND OF THE INVENTION

The present invention relates to a new and distinct cultivar of *Spiraea* plant, botanically known as *Spiraea media* and hereinafter referred to by the name 'SMSMBK'.

The new *Spiraea* plant is a product of a planned breeding program conducted by the Inventor in Grand Haven, Mich. The objective of the breeding program is to develop new compact and mounding *Spiraea* plants with attractive foliage and flowers and resistance to mildew pathogens.

The new *Spiraea* plant originated from an open-pollination during the summer of 2007 of *Spiraea media* 'SSBLUE', not patented, as the female, or seed, parent with an unknown selection of *Spiraea media*, as the male, or pollen, parent. The new *Spiraea* plant was discovered and selected by the Inventor during the summer of 2009 as a single flowering plant within the progeny of the stated open-pollination in a controlled environment in Grand Haven, Mich.

Asexual reproduction of the new *Spiraea* plant by softwood cuttings in a controlled greenhouse environment in Grand Haven, Mich. since the summer of 2009 has shown that the unique features of this new *Spiraea* plant are stable and reproduced true to type in successive generations of asexual reproduction.

SUMMARY OF THE INVENTION

Plants of the new *Spiraea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMSMBK'. These characteristics in combination distinguish 'SMSMBK' as a new and distinct *Spiraea* plant:

1. Compact, upright, outwardly spreading and mounding plant habit.
2. Vigorous growth habit.
3. Freely branching habit; dense and bushy habit.
4. Leaves that are initially greyed orange in color and become medium green with a greyed green-colored overlay with development.
5. Large inflorescences with white-colored flowers.
6. Good garden performance.
7. Resistant to mildew pathogens.

Plants of the new *Spiraea* can be compared to plants of the female parent, 'SSBLUE'. Plants of the new *Spiraea* differ from plants of 'SSBLUE' in the following characteristics:

1. Plants of the new *Spiraea* are more compact than plants of 'SSBLUE'.
2. Plants of the new *Spiraea* and 'SSBLUE' differ slightly in leaf color.

Plants of the new *Spiraea* can be compared to plants of the *Spiraea media* 'Snow Storm', not patented. Plants of the new *Spiraea* differ from plants of 'Snow Storm' in the following characteristics:

1. Plants of the new *Spiraea* are more compact than plants of 'Snow Storm'.
2. Plants of the new *Spiraea* and 'Snow Storm' differ in leaf color.

BRIEF DESCRIPTION OF THE PHOTOGRAPHS

The accompanying colored photographs illustrate the overall appearance of the new *Spiraea* plant showing the colors as true as it is reasonably possible to obtain in colored reproductions of this type. Colors in the photographs may differ slightly from the color values cited in the detailed botanical description which accurately describe the colors of the new *Spiraea* plant.

The photograph on the first sheet is a side perspective view of typical plants of 'SMSMBK' grown in an outdoor nursery.

The photograph on the second sheet is a close-up view of typical developing and fully expanded leaves of 'SMSMBK'.

The photograph on the third sheet is a close-up view of a typical inflorescence of 'SMSMBK'.

DETAILED BOTANICAL DESCRIPTION

The aforementioned photographs and following observations, measurements and values describe plants of the new *Spiraea* grown in three-gallon containers and ground beds in an outdoor nursery and polyethylene-covered greenhouse in Grand Haven, Mich. during the spring and under cultural practices typical of commercial *Spiraea* production. Plants were two years old when the photographs and the description were taken. In the description, color references are made to The Royal Horticultural Society Colour Chart, 1995 Edition, except where general terms of ordinary dictionary significance are used.

Botanical classification: *Spiraea media* 'SMSMBK'.

Parentage:

*Female, or seed, parent.*—*Spiraea media* 'SSBLUE', not patented.

*Male, or pollen, parent.*—Unknown selection of *Spiraea media*, not patented.

Propagation:

*Type.*—By softwood cuttings.

*Time to initiate roots, summer.*—About 15 days at temperatures about 22° C.

*Time to produce a rooted young plant, summer.*—About two months at temperatures about 22° C.

*Root description.*—Fine to thick, fibrous; cream to brown in color.

*Rooting habit.*—Freely branching; dense.

Plant description:

*Plant form and growth habit.*—Perennial shrub; compact, upright, outwardly spreading and mounding plant habit; vigorous growth habit.

*Branching habit.*—Freely branching habit with about 50 lateral branches developing per plant; pinching (removal of terminal apices) will enhance lateral branch development; dense and bushy habit.

*Plant height.*—About 40 cm to 60 cm.

*Plant diameter* (*area of spread*).—About 60 cm to 80 cm.

Lateral branch description:

*Length.*—About 50 cm.

*Diameter.*—About 2 mm to 4 mm.

*Internode length.*—About 3.5 cm.

*Texture.*—Smooth, glabrous.

*Color, developing.*—Close to 144D; distally, close to 185A.

*Color, developed.*—Close to 166A and 200A.

Leaf description:

*Arrangement.*—Alternate or whorled; simple.

*Length.*—About 2 cm to 6.5 cm.

*Width.*—About 1.5 cm to 4 cm.

*Shape.*—Broadly ovate.

*Apex.*—Acute.

*Base.*—Cuneate.

*Margin.*—Serrulate.

*Texture, upper surface.*—Smooth, glabrous; glaucous.

*Texture, lower surface.*—Slightly pubescent; glaucous.

*Venation pattern.*—Pinnate.

*Color.*—Developing leaves, upper and lower surfaces: Close to 137C; towards the apex, close to 176A. Fully expanded leaves, upper surface: Close to 137B overlain with close to 189A; venation, close to 145A; color becoming closer to 137B with development. Fully expanded leaves, lower surface: Close to 191A; venation, close to 145A.

*Petioles.*—Length: About 3 mm to 4 mm. Diameter: About 0.5 mm. Texture, upper and lower surfaces: Smooth, glabrous. Color, upper and lower surfaces: Close to 145A.

Flower description:

*Flower appearance and arrangement.*—Single rotate flowers arranged in terminal corymbs; freely flowering habit with usually about 200 flowers per inflorescence; flowers face upright to outwardly.

*Natural flowering season.*—Continuous flowering from late spring through the summer in Michigan; flowers not persistent.

*Fragrance.*—Mild, sweet.

*Inflorescence height.*—About 3 cm.

*Inflorescence diameter.*—About 4 cm to 5 cm.

*Flower diameter.*—About 5 mm.

*Flower length* (*height*).—About 3 mm.

*Flower buds.*—Length: About 1 mm to 1.5 mm. Diameter: About 1 mm to 1.5 mm. Shape: Globose. Color: Close to 144B.

*Petals.*—Quantity and arrangement: Five in a single whorl. Length: About 2 mm. Width: About 2 mm. Shape: Broadly obovate. Apex: Broadly obtuse to reuse. Margin: Entire. Texture, upper and lower surfaces: Smooth, glabrous. Color: When opening, upper and lower surfaces: Close to 155D. Fully opened, upper and lower surfaces: Close to 155D.

*Sepals.*—Quantity and arrangement: Five in a single whorl. Length: About 1 mm. Width: About 1 mm. Shape: Subulate. Apex: Acute. Base: Fused. Margin: Entire. Texture, upper and lower surfaces: Smooth, glabrous. Color: When opening and fully opened, upper surface: Close to 145A; towards the apex, close to 144A. When opening and fully opened, lower surface: Close to 144C; towards the apex, close to 141B. Fully opened, lower surface: Close to 54A.

*Peduncles.*—Length: About 30 cm to 35 cm. Diameter: About 1 mm to 2 mm. Strength: Strong. Aspect: Upright to outwardly. Texture: Smooth, glabrous. Color: Close to 144A.

*Pedicels.*—Length: About 1 mm to 2 mm. Diameter: About 0.5 mm. Strength: Strong. Aspect: Upright to outwardly. Texture: Smooth, glabrous. Color: Close to 144A.

*Reproductive organs.*—Androecium: Quantity per flower: About 25. Anther shape: Globose. Anther length: About 0.25 mm. Anther color: Close to 155B. Amount of pollen: Scarce. Pollen color: Close to 155B. Gynoecium: Quantity per flower: Five to twelve. Pistil length: About 1 mm. Style length: About 0.5 mm. Style color: Close to 155D. Stigma shape: Globose. Stigma color: Close to 155D. Ovary color: Close to 144C.

*Seeds and fruits.*—Seed and fruit development has not been observed on plants of the new *Spiraea*.

Garden performance: Plants of the new *Spiraea* have been observed to have good garden performance and to tolerate rain, wind and temperatures ranging from about −31° C. to about 38° C.

Pathogen & pest resistance: Plants of the new *Spiraea* have been observed to be resistant to mildew pathogens. Plants of the new *Spiraea* have not been observed to be resistant to pests and other pathogens common to *Spiraea* plants.

It is claimed:

1. A new and distinct *Spiraea* plant named 'SMSMBK' as illustrated and described.

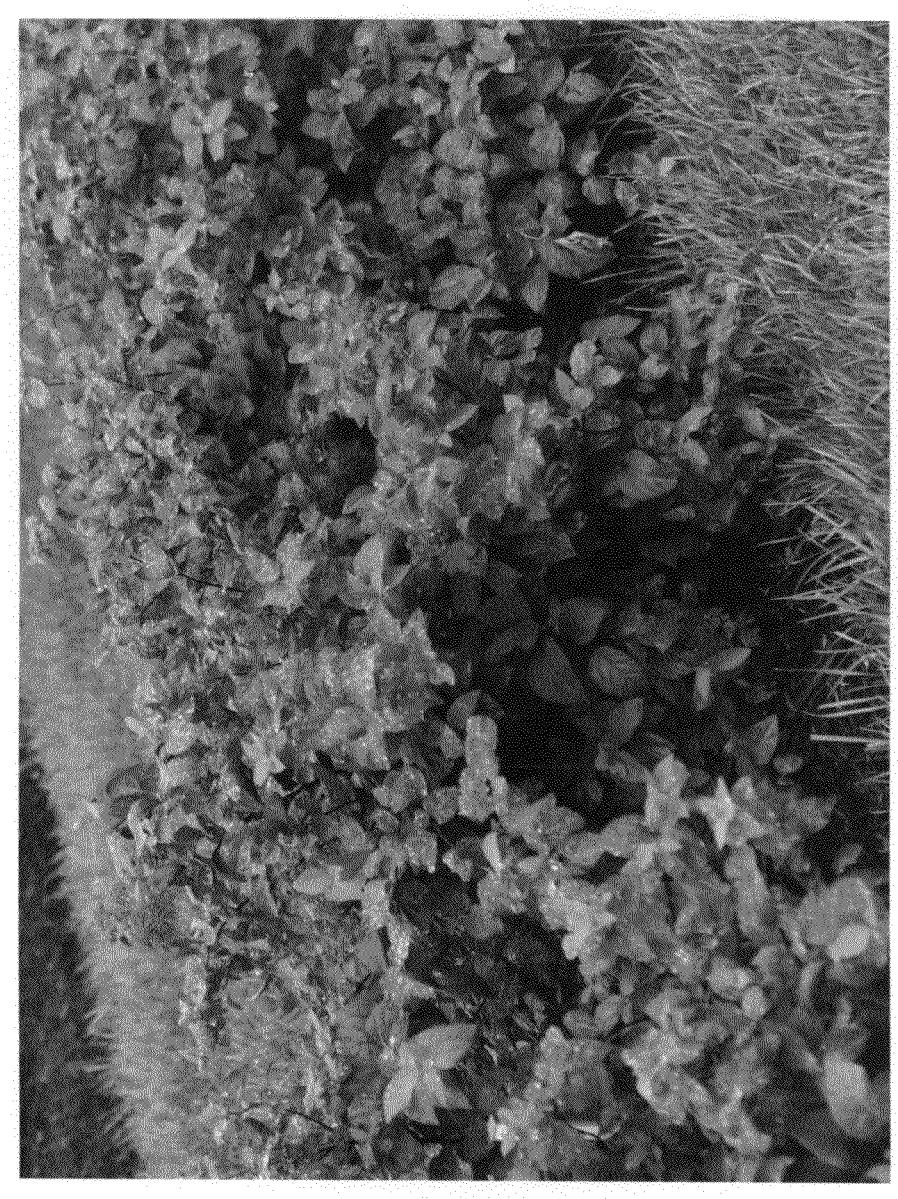

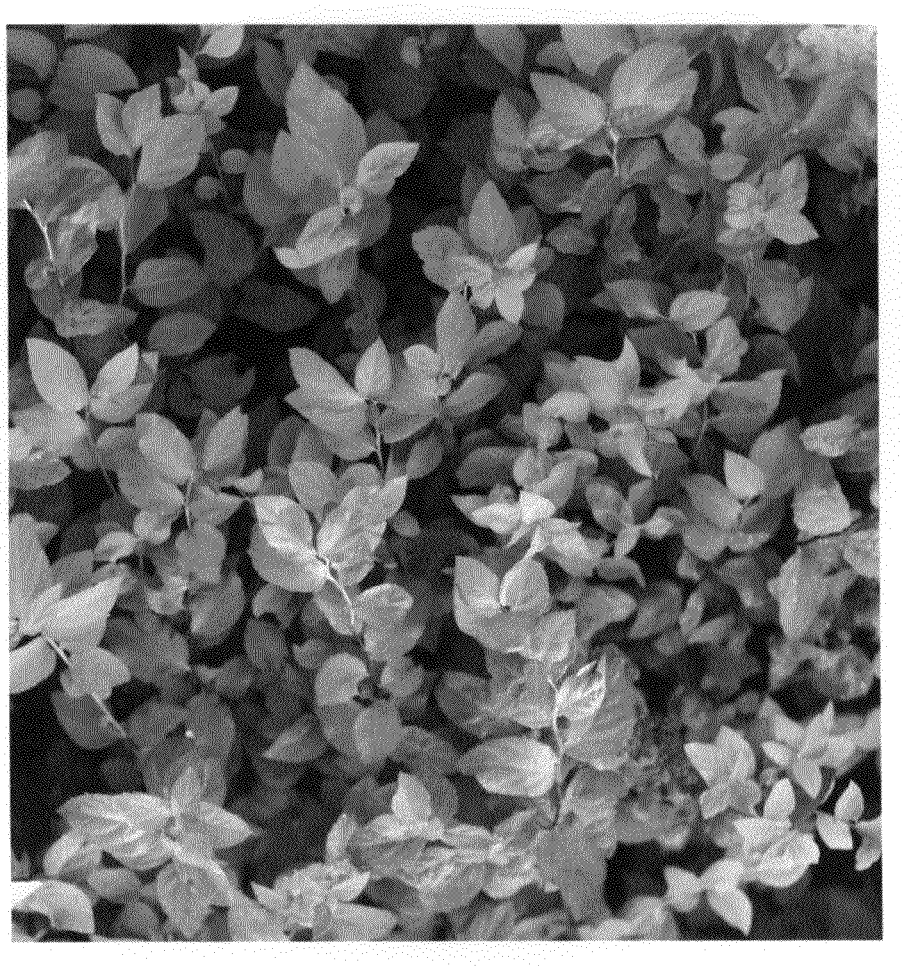

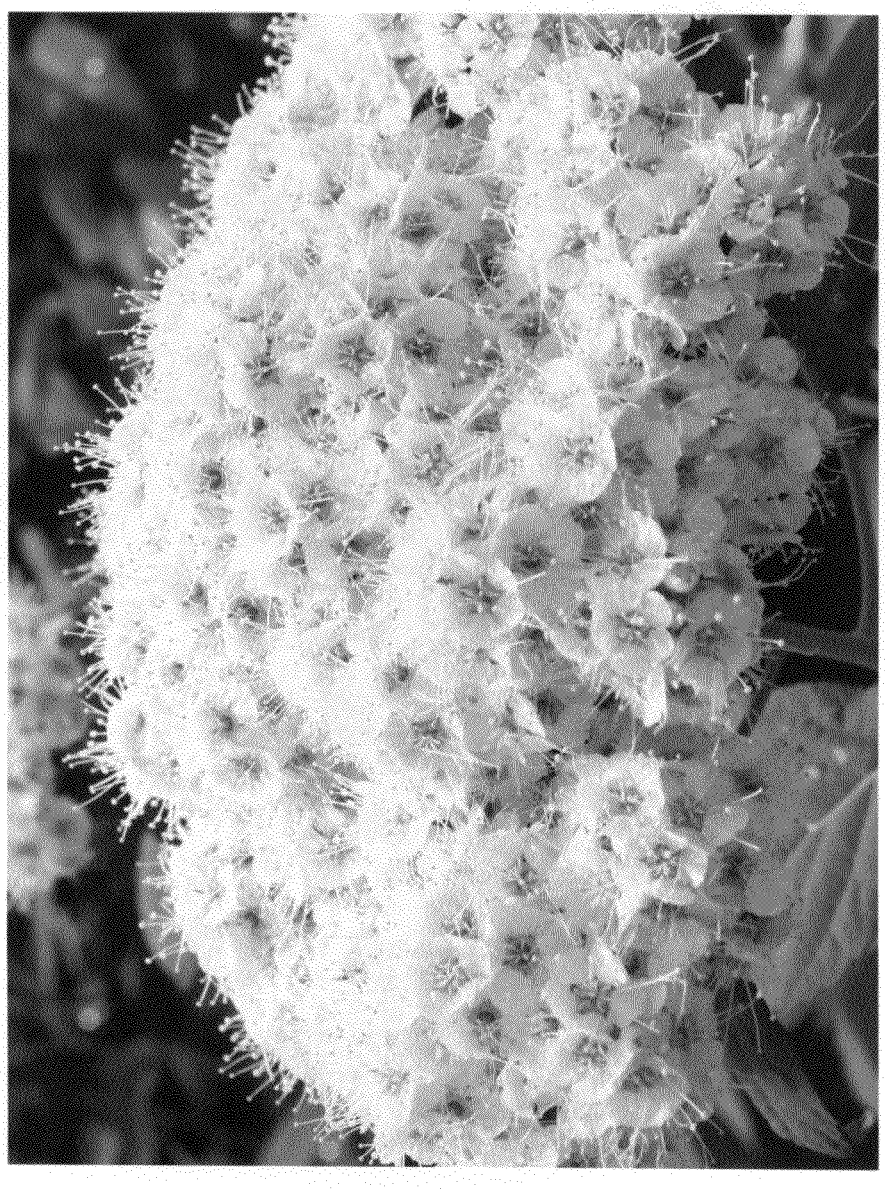

* * * * *